(12) United States Patent  (10) Patent No.: US 8,639,316 B2
Sarkar  (45) Date of Patent: Jan. 28, 2014

(54) METHOD AND APPARATUS FOR NOISE REJECTION IN ATRIAL ARRHYTHMIA DETECTION

(75) Inventor: Shantanu Sarkar, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 203 days.

(21) Appl. No.: 13/050,112

(22) Filed: Mar. 17, 2011

(65) Prior Publication Data

US 2012/0238892 A1 Sep. 20, 2012

(51) Int. Cl.
*A61B 5/0452* (2006.01)

(52) U.S. Cl.
USPC ............ 600/515; 600/519; 600/508; 600/509

(58) Field of Classification Search
USPC .................................. 600/508–528
See application file for complete search history.

(56) References Cited

U.S. PATENT DOCUMENTS

| | | | |
|---|---|---|---|
| 5,987,352 A | 11/1999 | Klein | |
| 6,230,059 B1 | 5/2001 | Duffin | |
| 6,397,100 B2 | 5/2002 | Stadler | |
| 6,522,915 B1 | 2/2003 | Ceballos | |
| 7,031,765 B2 | 4/2006 | Ritscher | |
| 7,289,847 B1 | 10/2007 | Gill | |
| 7,537,569 B2 | 5/2009 | Sarkar | |
| 7,623,911 B2 | 11/2009 | Sarkar | |
| 7,627,368 B2 | 12/2009 | Houben | |
| 7,853,317 B2 | 12/2010 | Duann | |
| 2003/0109792 A1 | 6/2003 | Hsu et al. | |
| 2004/0158295 A1* | 8/2004 | Dyjach et al. | 607/25 |
| 2004/0193066 A1* | 9/2004 | Carlson et al. | 600/509 |
| 2004/0215240 A1 | 10/2004 | Lovett et al. | |
| 2005/0038351 A1 | 2/2005 | Starobin et al. | |
| 2005/0070965 A1 | 3/2005 | Kil et al. | |
| 2007/0173894 A1 | 7/2007 | Li | |
| 2007/0239050 A1 | 10/2007 | Ghanem et al. | |
| 2008/0161703 A1 | 7/2008 | Houben et al. | |
| 2010/0114241 A1 | 5/2010 | Donofrio et al. | |
| 2010/0312131 A1 | 12/2010 | Naware | |

OTHER PUBLICATIONS (PCT/US2012/022342) PCT Notification of Transmittal of the International Search Report and the Written Opinion of the International Searching Authority, 2012.

* cited by examiner

*Primary Examiner* — Joseph Stoklosa
(74) *Attorney, Agent, or Firm* — Michael C. Soldner (57) ABSTRACT

A medical device performs a method for determining a cardiac event by obtaining a signal comprising cardiac cycle length information in a patient and determining cardiac cycle lengths during an established time interval. Noise is detected during the time interval and a cardiac cycle length corresponding to a time of the detected noise is rejected. Cycle length differences are determined from the cycle lengths not rejected during the time interval. The cardiac event is determined in response to the cycle length differences.

21 Claims, 9 Drawing Sheets

METHOD AND APPARATUS FOR NOISE REJECTION IN ATRIAL ARRHYTHMIA DETECTION

TECHNICAL FIELD

The disclosure relates generally to implantable medical devices and, in particular, to methods for detecting atrial arrhythmias using ventricular cycle lengths.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

In the past, atrial arrhythmias have been largely undertreated due to the perception that these arrhythmias are relatively benign. As more serious consequences of persistent atrial arrhythmias have come to be understood, such as an associated risk of relatively more serious ventricular arrhythmias and stroke, there is a growing interest in monitoring and treating atrial arrhythmias.

Methods for discriminating arrhythmias that are atrial in origin from arrhythmias originating in the ventricles have been developed for use in dual chamber implantable devices wherein both an atrial EGM signal and a ventricular EGM signal are available. Discrimination of arrhythmias can rely on event intervals (PP intervals and RR intervals), event patterns, and EGM morphology. Such methods have been shown to reliably discriminate ventricular arrhythmias from supraventricular arrhythmias. However, in single chamber implantable devices, subcutaneous implantable devices, and external monitoring devices, an adequate atrial EGM signal having acceptable signal-to-noise ratio is not always available for use in detecting and discriminating atrial arrhythmias.

DETAILED DESCRIPTION

In the following description, references are made to illustrative embodiments for carrying out the methods described herein. It is understood that other embodiments may be utilized without departing from the scope of the disclosure.

In various embodiments, ventricular signals are used for determining successive ventricular cycle lengths for use in detecting atrial arrhythmias. The atrial arrhythmia detection methods do not require an atrial signal source. The methods presented herein may be embodied in software, hardware or firmware in implantable or external medical devices. Such devices include implantable monitoring devices having cardiac EGM/ECG monitoring capabilities and associated EGM/ECG sense electrodes, which may be intracardiac, epicardial, or subcutaneous electrodes.

The methods described herein can also be incorporated in implantable medical devices having therapy delivery capabilities, such as single chamber or bi-ventricular pacing systems or ICDs that sense the R-waves in the ventricles and deliver an electrical stimulation therapy to the ventricles. The atrial arrhythmia detection methods presently disclosed may also be incorporated in external monitors having ECG electrodes coupled to the patient's skin to detect R-waves, e.g. Holter monitors, or within computerized systems that analyze pre-recorded ECG or EGM data. Embodiments may further be implemented in a patient monitoring system, such as a centralized computer system which processes data sent to it by implantable or wearable monitoring devices.

It is also recognized that various embodiments may be implemented in internal or external monitoring systems that include sensors of ventricular activity other than electrical signals from which ventricular cycle length (VCL) measurements can be made. Practice of these methods is therefore not limited to the use of EGM or ECG signals for measuring VCLs. Other signals, such as pressure signals, blood oximetry signals, flow signals, ventricular wall motion signals, volume-related impedance signals, or other physiological signals responsive to the ventricular cycle, can be used for measuring VCLs. Generally, VCL measurements should have a resolution on the order of about 1 to 20 ms to allow for atrial arrhythmia detection based on VCL irregularity metrics, however, aspects of the presently disclosed methods may be implemented in systems having lower resolution of VCL measurements.

Figure 1:
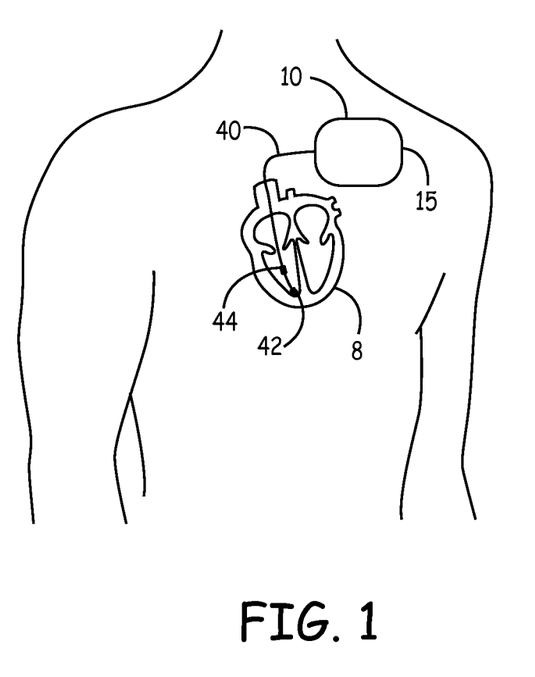
FIG. 1 is an illustration of an implantable medical device (IMD) implanted in a patient and coupled to the patient's heart via a ventricular lead.

FIG. 1 is an illustration of an implantable medical device (IMD) implanted in a patient and coupled to the patient's heart via a ventricular lead. The simplified illustration of IMD 10 may represent a variety of IMDs such as a cardiac pacemaker, implantable cardioverter defibrillator, hemodynamic monitor, ECG recorder, or a drug delivery device. IMD 10 may be coupled to one or more fluid delivery catheters or electrical leads 20. In the embodiment shown, lead 40 is used for carrying one or more electrodes and/or other physiological sensors used for monitoring one or more physiological signals and delivering electrical stimulation therapies to the patient's heart 8. IMD 10 may alternatively be embodied as a leadless device wherein sensors and/or electrodes are incorporated in or on the housing of IMD 10. Examples of devices incorporating leadless electrodes are generally disclosed in U.S. Pat. No. 6,522,915 (Ceballos et al.) and U.S. Pat. No. 5,987,352 (Klein et al.), both of which patents are incorporated herein by reference in their entirety.

Lead 40 is a right ventricular lead including one or more electrodes 42 and/or sensors 44. Electrode 42 may be used in conjunction with IMD housing 15 for sensing ventricular EGM signals. Lead 40 may be provided with a second electrode for bipolar sensing of EGM signals. In one embodiment, sensor 44 is used for sensing a ventricular pressure signal, or other signal correlated to the cyclical ventricular activity, which may be used in some embodiments for determining VCLs.

Figure 2:
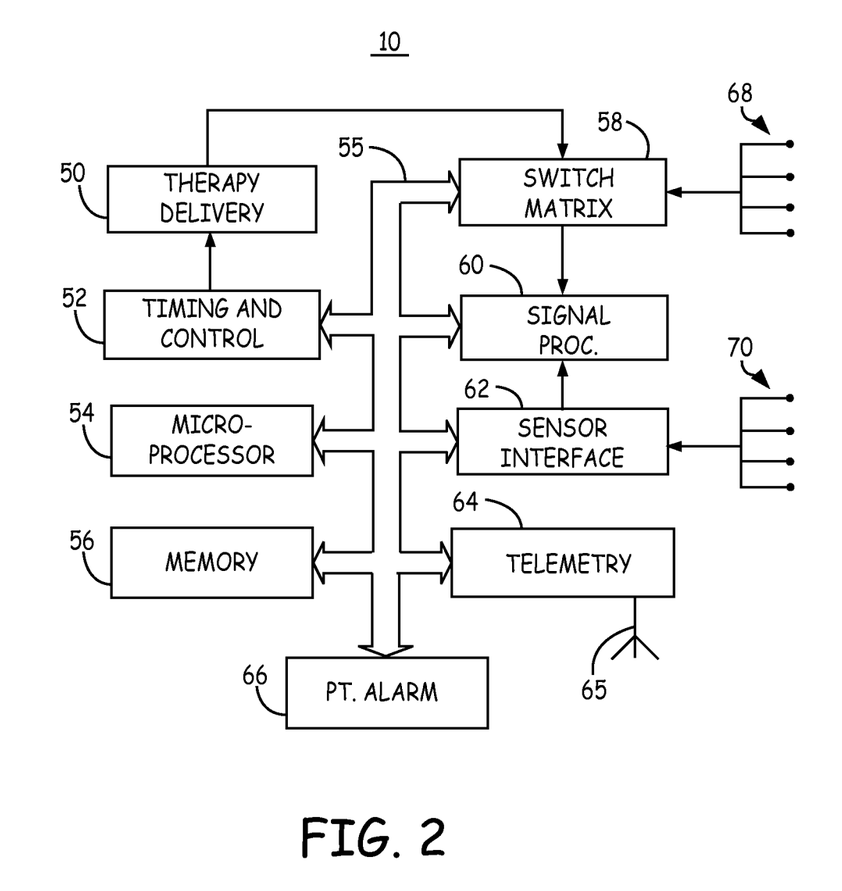
FIG. 2 is a functional block diagram of an IMD according to one embodiment.

FIG. 2 is a functional block diagram of IMD 10. IMD 10 generally includes timing and control circuitry 52 and an operating system that may employ microprocessor 54 or a digital state machine for timing sensing and therapy delivery functions and controlling other device functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may be lead-based electrodes, leadless electrodes incorporated on IMD 10, and/or the IMD housing configured for use as a can or case electrode. Electrodes 68 are used for sensing electrical ventricular signals and may be used for sensing other signals within the body, such as impedance signals. Cardiac electrical signals are sensed using any of electrodes 68 for detecting and diagnosing heart rhythms and may be used for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias.

IMD 10 may include other physiological sensors 70. Physiological sensors 70 may include pressure sensors, accelerometers, flow sensors, blood chemistry sensors, activity sensors or other implantable physiological sensors. Sensors 70 are coupled to IMD 10 via a sensor interface 62 which provides sensor signals to signal processing circuitry 60. Sensor interface 62 may include integrated circuitry for providing sensor drive signals or excitation signals to sensors 70 and for receiving a raw signal and converting to an analog or digital sensor signal for sensing physiological events. Sensor signals are used by microprocessor 54 for detecting physiological events or conditions. For example, IMD 10 may monitor heart wall motion, blood pressure, blood chemistry, respiration, or patient activity. Monitored signals may be used for diagnosing a patient condition or for sensing the need for delivering or adjusting a therapy under control of the operating system.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. Memory 56 is used to store operating commands and data for controlling device operation and for later retrieval to diagnose device function or patient condition. In accordance with the various embodiments, parameter values and thresholds used for detecting atrial arrhythmias from a ventricular signal are stored in memory 56. A portion of memory 56 is allocated for storing ventricular cycle length data over predetermined intervals of time and used for determining a metric of VCL irregularity as will be described herein.

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit. Data from IMD 10 may be transmitted to a centralized patient database to enable a physician to monitor the patient from a remote location.

IMD 10 may include patient alarm circuitry 66 for generating audible tones, a perceptible vibration, muscle stimulation or other sensory stimulation for notifying the patient that an alarm condition has been detected by IMD 10.

Figure 3:
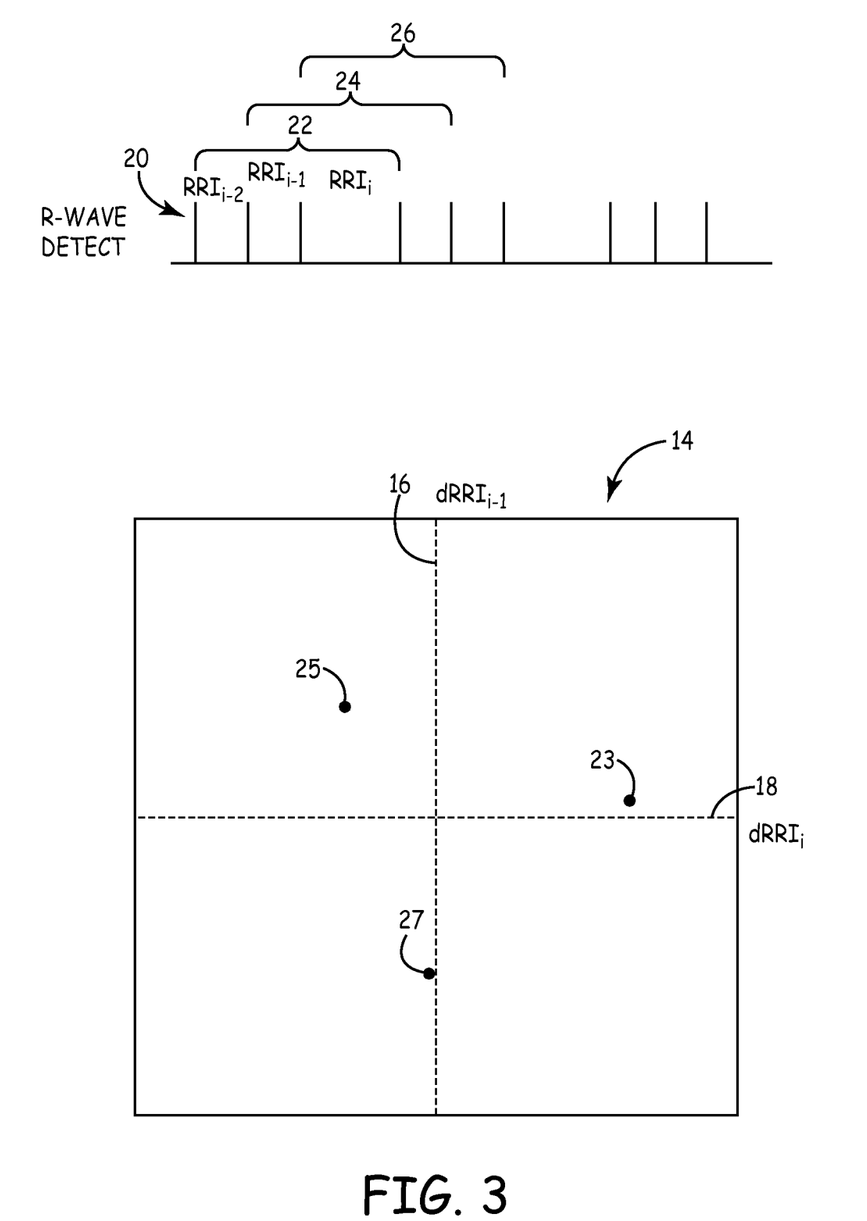
FIG. 3 illustrates the generation of a Lorenz scatter plot of VCL data for use in detecting atrial arrhythmias.

FIG. 3 illustrates the generation of a Lorenz scatter plot of VCL data for use in detecting atrial arrhythmias. The differences between consecutive RR intervals ($\delta$RRs) are plotted for a time series of R-R intervals (RRIs). The Lorenz plot 14 is a Cartesian coordinate system defined by $\delta RR_i$ along the x-axis 18 and $\delta RR_{i-1}$ along the y-axis 16. As such, each plotted point in a Lorenz plot is defined by an x-coordinate equaling $\delta RR_i$ and a y-coordinate equaling $\delta RR_{i-1}$. $\delta RR_i$ is the difference between the $i^{th}$ RRI and the previous RRI, $RRI_{i-1}$. $\delta RRI_{i-1}$ is the difference between $RRI_{i-1}$ and the previous RRI, $RRI_{i-2}$. As such, each data point plotted on the Lorenz plot 14 represents a VCL pattern relating to three consecutive VCLs: $RRI_i$, and $RRI_{i-2}$, measured between four consecutively sensed R-waves. As noted previously, VCL information is not limited to detection of R-waves and determination of RRIs. The terms RRI and $\delta RR_i$ as used herein refer generally to a measurement of VCL and the difference between two consecutive VCL measurements, respectively, whether the VCL measurements were derived from a series of R-wave detections from an EGM or ECG signal or another ventricular cycle event detection from any other physiological signal (e.g. a peak pressure determined from a pressure signal). For the sake of illustration, the embodiments described herein often refer to R-wave detections for performing VCL measurements and the determination of ($\delta RR_i$, $\delta RR_{i-1}$) points.

In FIG. 3, a series of R-wave events 20 are shown. In order to plot a point on the Lorenz plot area 14, a ($\delta RR_i$, $\delta RR_{i-1}$) point is determined by measuring successive RRIs determined from the R-wave events 20. In the example shown, a first series 22 of three consecutive RRIs ($RRI_{i-2}$, $RRI_{i-1}$ and $RRI_i$) provides the first data point on the Lorenz plot area 14. $\delta RR_{i-1}$, which is the difference between $RRI_{i-2}$ and $RRI_{i-1}$ is approximately 0. $\delta RR_i$, the difference between the $RRI_{i-1}$ and $RRI_i$, is a positive change. Accordingly, a ($\delta RR_i$, $\delta RR_{i-1}$) point 23 having a y-coordinate near 0 and a positive x-coordinate is plotted in the Lorenz plot 14, representing the first series 22.

The next series 24 of three RRIs provides the next ($\delta RR_i$, $\delta RR_{i-1}$) point 25 having a negative x-cooridinate ($RRI_i$ being less than $RRI_{i-1}$) and a positive y-coordinate ($RRI_{i-1}$ being greater than $RRI_{i-2}$). This process of plotting ($\delta RR_i$, $\delta RR_{i-1}$) points continues with the three cycle series 26 providing data point 27 and so on.

Methods have been developed for detecting atrial arrhythmias based on the irregularity of ventricular cycles measured by RR intervals that exhibit discriminatory signatures when plotted in a Lorenz scatter plot such as the plot shown in FIG. 3. One such method is generally disclosed by Ritscher et al. in U.S. Pat. No. 7,031,765, incorporated herein by reference in its entirety. Other methods are generally disclosed by Sarkar, et al. in U.S. Pat. Nos. 7,623,911 and in 7,537,569 and by Houben in U.S. Pat. No. 7,627,368, all of which patents are also incorporated herein by reference in their entirety.

Figure 4:
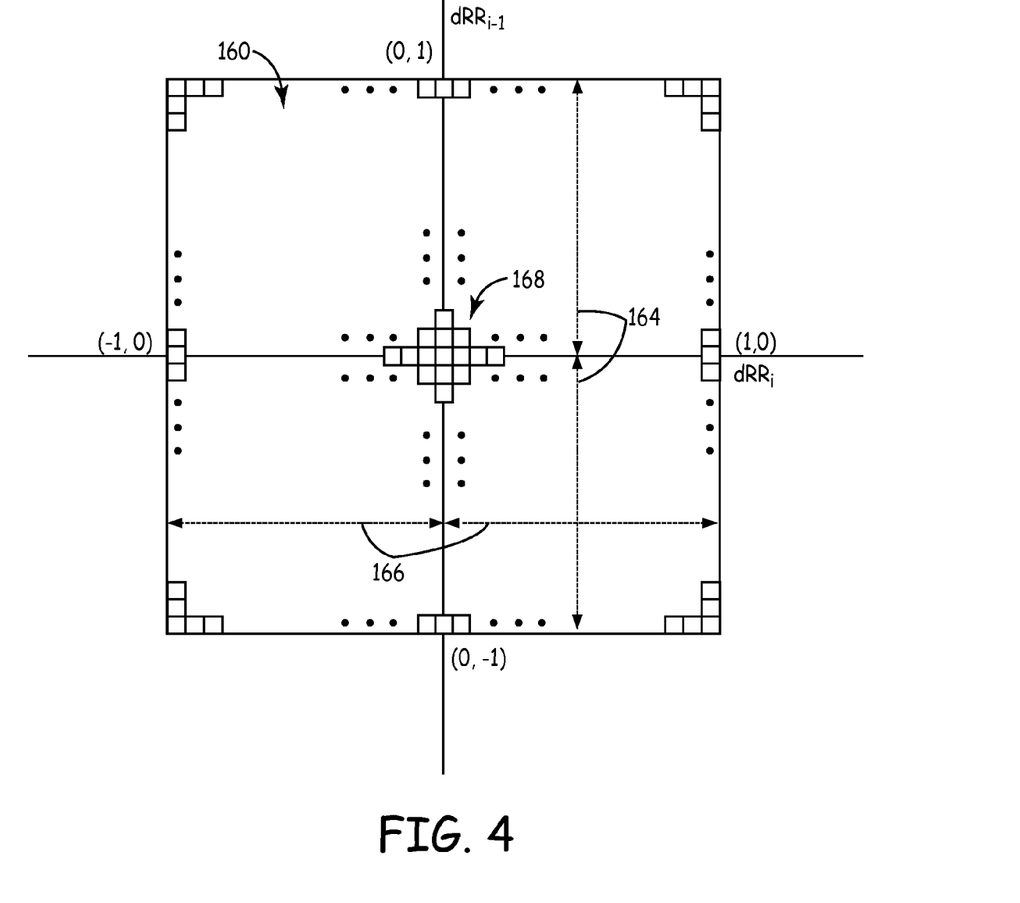
FIG. 4 is a diagram of a two-dimensional histogram representing the Lorenz plot area.

FIG. 4 is a diagram of a two-dimensional histogram representing the Lorenz plot area. Generally, the Lorenz plot area 14 shown in FIG. 3 is numerically represented by a two-dimensional histogram 160 having predefined ranges 166 and 164 in both positive and negative directions for the $\delta RR_i$ and $\delta RR_{i-1}$ coordinates, respectively. The two-dimensional histogram is divided into bins 168 each having a predefined range of $\delta RR_i$ and $\delta RR_{i-1}$ values. In one example, the histogram range might extend from –1200 ms to +1200 ms for both $\delta RR_i$ and $\delta RR_{i-1}$ values, and the histogram range is divided into bins extending 7.5 ms in each of the two dimensions resulting in a 160 bin×160 bin histogram. The successive RRI differences determined over a detection time interval are used to populate the histogram 160. Each bin stores a count of the number of ($\delta RR_i$, $\delta RR_{i-1}$) data points falling into the bin range. The bin counts may then be used in determining RRI variability metrics and patterns for determining a cardiac rhythm type.

At times, non-ventricular signal noise may corrupt the ventricular signal. Noise may be incorrectly sensed as an R-wave resulting in erroneous RRI measurements. Two RRIs will be measured in association with each sensed event, one RRI ending with the sensed event and the one beginning with the sensed event. If the sensed event is actually noise, both the RRI ending with the sensed event and the RRI beginning with the sensed event will be RRIs that are associated with noise or artifact. These two RRIs could contribute to up to four ($\delta RR_i$, $\delta RR_{i-1}$) points.

Figure 5:
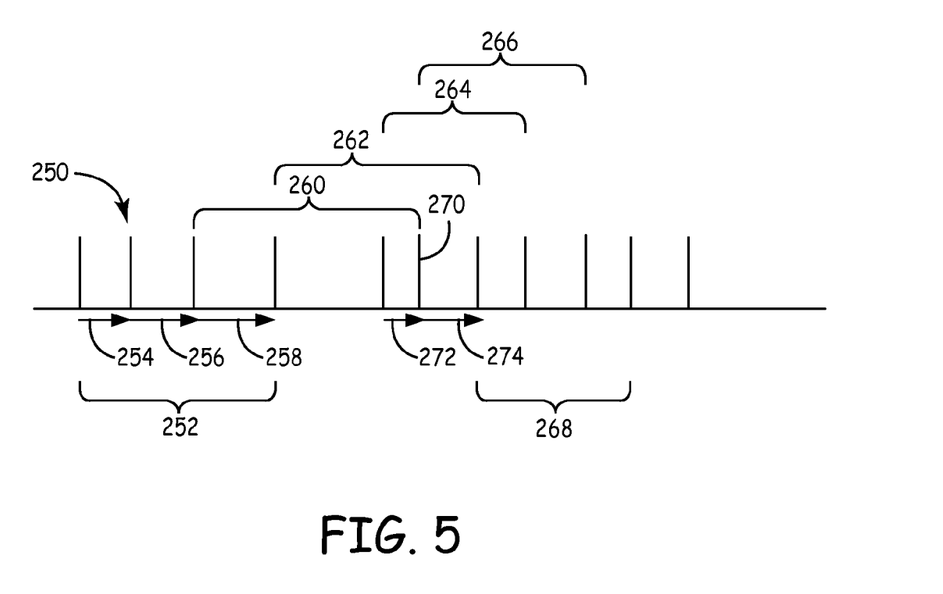
FIG. 5 is a depiction of a series of events sensed from a ventricular signal.

FIG. 5 is a depiction of a series of events 250 sensed from a ventricular signal. These sensed events 250 are each treated as R-waves and used to measure RRIs for determining ($\delta RR_i$, $\delta RR_{i-1}$) data points. The ($\delta RR_i$, $\delta RR_{i-1}$) data points will be used to populate a histogram for determining a cardiac rhythm. As described previously, each ($\delta RR_i$, $\delta RR_{i-1}$) data point involves four sensed events. For example, a series 252 of three RRIs 254, 256 and 258 would provide the successive RRI differences for one ($\delta RR_i$, $\delta RR_{i-1}$) data point.

A single sensed event 270 can be associated with four ($\delta RR_i$, $\delta RR_{i-1}$) data points. Event 270 will define a preceding RRI 272 and a succeeding RRI 274. These two RRIs 272 and 274 will be included in series 260, series 262, series 264 and series 266. Each of these series 260, 262, 264 and 266 of three successive RRIs are used to compute successive RRI differences that define four respective ($\delta RR_i$, $\delta RR_{i-1}$) data points.

If sensed event 270 is actually noise, up to four ($\delta RR_i$, $\delta RR_{i-1}$) data points determined using the series 260, 262, 264, and 266 involve the noise intervals 272 and 274. As will be further described below, when evidence of noise is detected, at least one RRI 272 or 274 associated with the noise evidence may be rejected. Any ($\delta RR_i$, $\delta RR_{i-1}$) data points using an RRI series 260, 262, 264 and 266 involving a rejected noise interval 272 or 274 may be skipped when populating the histogram defining a Lorenz plot area.

If both RRI 272 and RRI 274 are rejected due to event 270 being detected as noise, the first RRI series after series 252 used to populate a Lorenz plot area histogram would be series 268. Each of the other series 260, 262, 264 and 266 involve a rejected RRI 272 and 274. In some embodiments, only the short RRI 272 is rejected. In this case, the RRI series 266 involving RRI 274 would be used for determining a ($\delta RR_i$, $\delta RR_{i-1}$) data point.

Figure 6:
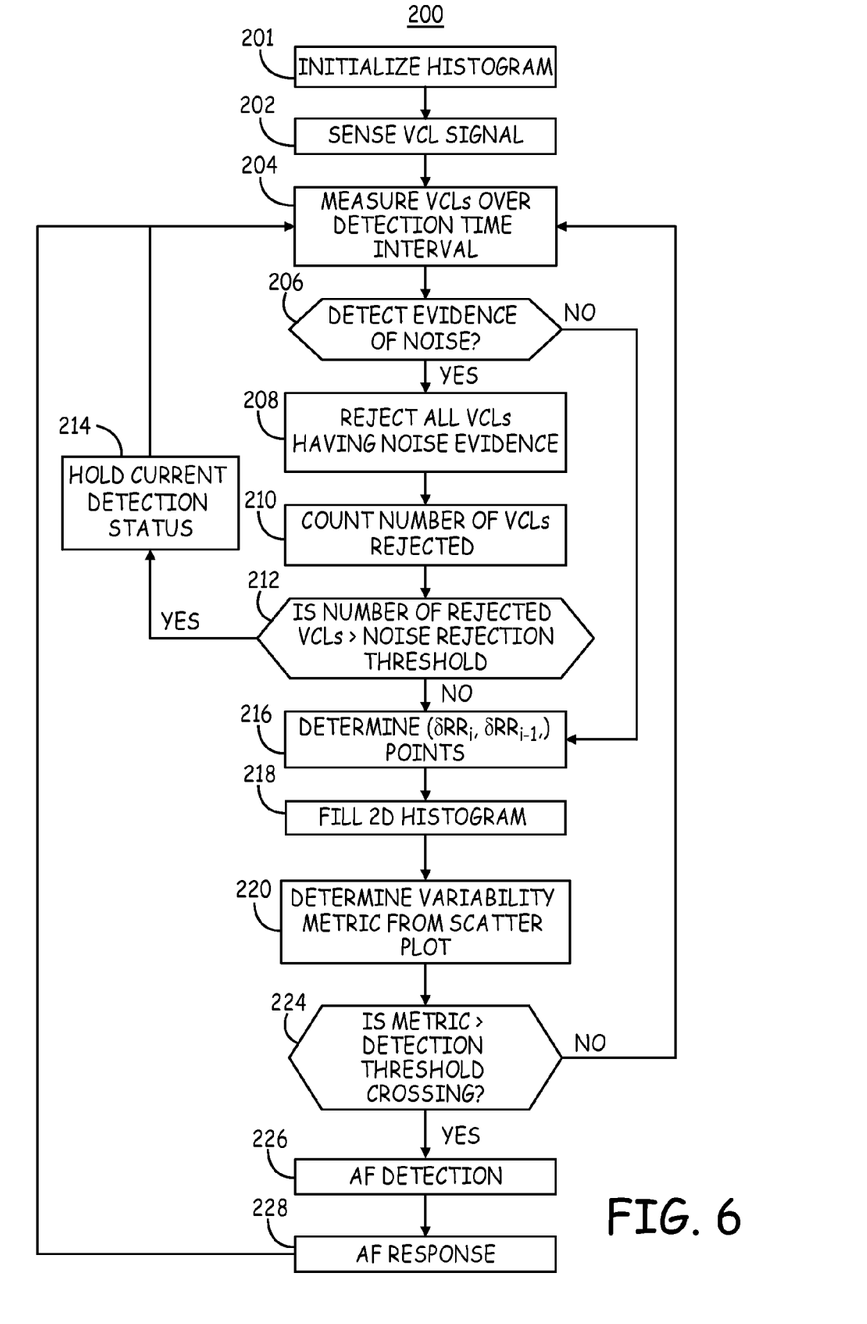
FIG. 6 is a flow chart of a method for detecting atrial fibrillation.

FIG. 6 is a flow chart of a method for detecting atrial fibrillation. Flow chart 200 and other flow charts presented herein are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Flow chart 200 is directed to atrial fibrillation (AF) detection, however it is recognized that aspects of the method may be applied to detection of other atrial arrhythmias, such as atrial flutter or other forms of atrial tachycardia. At block 201, a histogram is initialized by defining the number of histogram bins for each coordinate axis and corresponding bin ranges. A counter for each histogram bin is set to zero. At block 202, a physiological signal containing VCL information is obtained. The signal may be an EGM or ECG signal but is not limited to being a cardiac electrical signal.

At block 204 the VCL intervals, e.g. RRIs, are collected over a predetermined rhythm detection time interval, for example for 2 minutes. Data collected over the established detection time interval is used to classify the rhythm at the end of the detection time interval. At block 206, a noise detection analysis is performed to detect evidence that a sensed R-wave signal or measured RRI contains noise artifact. Numerous noise detection methods may be used. Evidence of noise may detected based on frequency content, amplitude content, or VCL measurements themselves.

If no evidence of noise is detected in the predetermined time interval, the ($\delta RR_i$, $\delta RR_{i-1}$) data points are computed from the measured VCLs at block 216. If evidence of noise is detected, the VCLs that are associated with noise evidence are rejected at block 208. Any ($\delta RR_i$, $\delta RR_{i-1}$) data points that involve an RRI that is rejected will be skipped. Depending on the noise detection method being used, evidence of noise may be detected during the RRI between sensed R-waves or a sensed R-wave itself may be detected as noise. If a sensed R-wave is determined to be noise, both the preceding and subsequent RRIs defined by the sensed R-wave may be rejected as noise intervals.

The number of rejected VCLs is counted at block 210. The total number of VCLs (e.g. RRIs) rejected during the detection time interval due to noise is compared to a noise rejection threshold at block 212. If the noise rejection threshold is exceeded, the current rhythm detection status is held at block 214. The current time interval is considered to be too noisy for use in rhythm detection and no change in the status of the currently detected rhythm will be made based on the VCLs measured during the current time interval. For example, if the IMD detected AF at the end of the last detection time interval based on the analysis of histogram counts, the AF detection will be maintained at the end of the current time interval. If the IMD is not detecting AF at the end of the previous detection time interval, the IMD remains in a state of no AF detection at the end of the current time interval. The current detection time interval is rejected as a whole for rhythm determination and classification. The process returns to block 204 to measure VCLs over the next detection time interval.

If the number of rejected cycle lengths has not reached a noise rejection threshold (block 212), the current detection time interval data is still used to populate a histogram defining a Lorenz plot area. At block 216, the ($\delta RR_i$, $\delta RR_{i-1}$) data points are determined using only RRIs that are not associated with noise evidence detection. Rejected RRIs are not used to compute RRI differences or ($\delta RR_i$, $\delta RR_{i-1}$) data points determined using rejected RRIs are skipped when populating the histogram. In this way, RRIs associated with noise aren't included in the analysis of VCLs in the Lorenz plot histogram. The remainder of the VCLs that are not rejected during the detection time interval are used for determining ($\delta RR_i$, $\delta RR_{i-1}$) data points. All ($\delta RR_i$, $\delta RR_{i-1}$) data points points not involving a rejected RRI may be used to populate the histogram. If a non-rejected VCL is sandwiched between two rejected VCLs, the VCL is not used because no adjacent non-rejected VCL is available for computing consecutive RRI differences for determining a valid ($\delta RR_i$, $\delta RR_{i-1}$) data point.

As described previously, a 2D scatter plot is generated wherein each point is defined by an x-coordinate corresponding to the difference between an RRI and the previous RRI and the y-coordinate corresponding to the difference between the previous RRI and the next previous RRI. The histogram is filled by incrementing a counter for the histogram bin which corresponds to the coordinate values of each ($\delta RR_i$, $\delta RR_{i-1}$) data point. The methods described herein are generally implemented using a 2D histogram, however aspects of the invention may alternatively be implemented in methods using 1D or higher dimensional scatter plots of VCL data.

At block 220 an RRI variability metric (or more generally a VCL variability metric) is determined from the scatter plot. Generally, the more histogram bins that are occupied, i.e. the more sparse the distribution of ($\delta RR_i$, $\delta RR_{i-1}$) points, the more irregular the VCL during the data acquisition time period. As such, a metric of the RRI variability can be used for detecting atrial fibrillation, which is associated with highly irregular VCL. In one embodiment, an RRI variability metric for detecting AF, referred to as an AF score is computed as generally described in the above-incorporated '911 patent. Briefly, the AF score may be defined by the equation:

AF Evidence=Irregularity Evidence−Origin Count−PAC Evidence wherein Irregularity Evidence is the number of occupied histogram bins outside a Zero Segment defined around the origin of the Lorenz plot area. During normal sinus rhythm or highly organized atrial tachycardia, nearly all points will fall into the Zero Segment because of relatively small, consistent differences between consecutive RRIs. A high number of occupied histogram bins outside the Zero segment is therefore positive evidence for AF.

The Origin Count is the number of points in a "Zero Segment" defined around the Lorenz plot origin. A high Origin Count indicates regular RRIs, a negative indicator of AF, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with PACs that occur at regular coupling intervals and present regular patterns of RRIs, e.g. associated with bigeminy (short-short-long RRIs) or trigeminy (short-short-short-long RRIs).

In other embodiments, an AF score or other RRI variability score for classifying an atrial rhythm may be computed as described in any of the above-incorporated '765, '911, '569 and '368 patents.

The AF score will be compared to a threshold for detecting AF at block 224. If the metric crosses a detection threshold, AF detection is made at block 226. A response to AF detection is made at block 228, which may include withholding a ventricular therapy, storing data, triggering other signal acquisition or analysis. The AF response may be to generate a patient alarm or deliver or adjust a therapy. The RRI measurements continue to be performed after an AF detection to fill the histogram during the next detection time interval by returning to block 204.

After each detection time interval, the RRI variability metric is determined and the histogram bins are re-initialized to zero for the next detection time interval. The new RRI variability metric determined at the end of each data acquisition interval may be used to determine if the AF episode is sustained or terminated.

Figure 7:
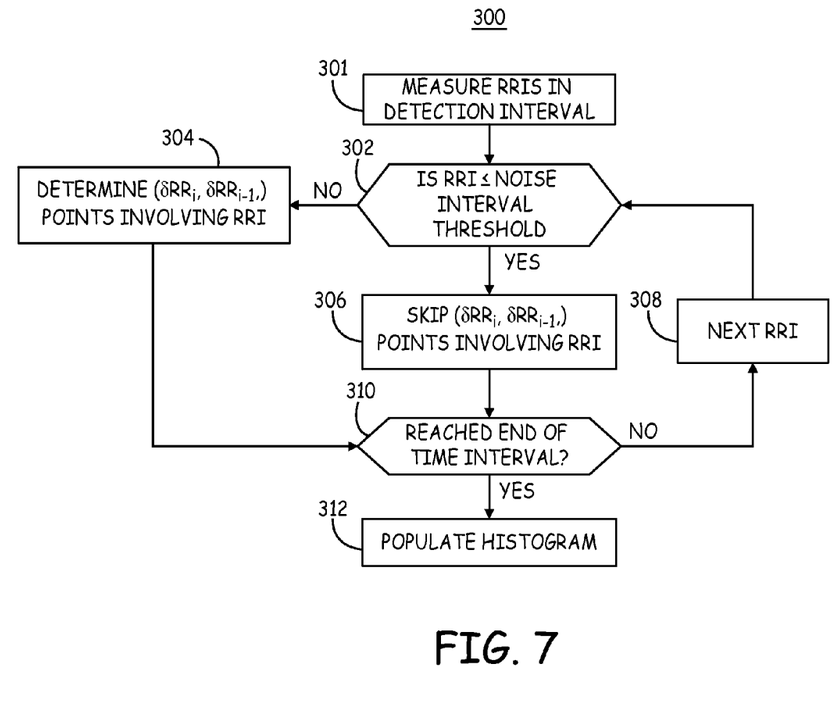
FIG. 7 is a flow chart of one method for detecting evidence of noise for use in rejecting VCLs associated with noise.

FIG. 7 is a flow chart 300 of one method for detecting evidence of noise for use in rejecting VCLs associated with noise. Flow chart 300 is described with reference to RRIs as measured VCLs, however, it is recognized that other intervals from either cardiac electrical or other cardiac signals may be measured to determine VCLs. At block 301, all RRIs are measured during an established detection time interval. At block 302, each RRI is compared to a noise interval threshold. If the RRI is less than or equal to a noise interval threshold, this RRI is determined to be evidence of noise. In one embodiment, a noise interval threshold is approximately 220 ms. All ($\delta RR_i$, $\delta RR_{i-1}$) data points that involve an RRI detected as noise are skipped or ignored as indicated at block 306.

All RRIs that are greater than the noise interval threshold can be used for determining ($\delta RR_i$, $\delta RR_{i-1}$) points at block 304, as long as the adjacent RRIs needed for computing RRI differences are also not rejected. After either accepting or rejecting each RRI, the process advances to the next RRI at block 308 until the end of the detection time interval is reached as determined at block 306. If the end of the detection time interval is reached at decision block 310, the ($\delta RR_i$, $\delta RR_{i-1}$) data points determined using only RRIs that are longer than the noise rejection threshold are used to generate the histogram at block 312 as described previously. In summary, in one embodiment detecting evidence of noise includes measuring RRIs (or VCLs). If an RRI is shorter than a noise interval threshold, the RRI is rejected. Any ($\delta RR_i$, $\delta RR_{i-1}$) data points involving a rejected RRI are skipped or ignored when incrementing Lorenz plot histogram bin counts for a detection time interval.

Figure 8:
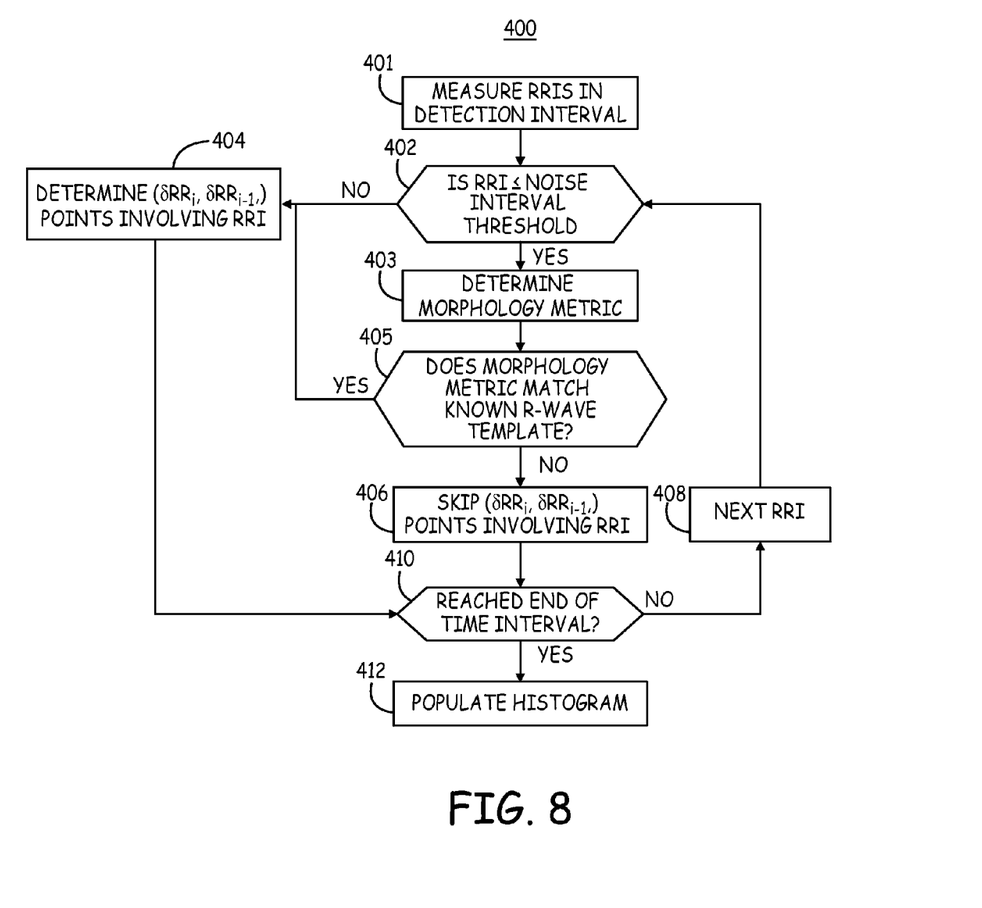
FIG. 8 is a flow chart of an alternative method for detecting evidence of noise for use in rejecting VCLs.

FIG. 8 is a flow chart 400 of an alternative method for detecting evidence of noise for use in rejecting VCLs. At block 410, RRIs are measured during a detection time interval, and each RRI is compared to a noise interval threshold at block 402. If the RRI is greater than the noise interval, it can be used in determining ($\delta RR_i$, $\delta RR_{i-1}$) data points at block 404.

In response to an RRI that is less than or equal to a noise interval threshold, a morphology analysis is performed at blocks 403 and 405. A morphology metric or template of at least the sensed R-wave ending the short RRI and optionally both the beginning and ending R-waves of the short RRI, is determined at block 403. A morphology metric may be a waveform template, an amplitude, slope, R-wave width, R-wave area, or other morphology-related feature of the sensed R-wave signal.

The morphology metric is compared to a template metric established for a known R-wave at block 405. If a morphology metric for a sensed R-wave approximately matches a morphology metric of a known R-wave signal, the associated RRI is not detected as a noisy interval and is not rejected. The RRI is used for determining ($\delta RR_i$, $\delta RR_{i-1}$) data points at block 404.

If, however, the morphology metric does not approximately match a known R-wave template value for the metric, as determined at decision block 405, the short RRI is detected as noise. The short RRI is rejected and ($\delta RR_i$, $\delta RR_{i-1}$) data points involving the rejected RRI are skipped or ignored, as indicated at block 406.

If the end of the detection time interval has not been reached, the process continues to the next RRI at block 408. Upon reaching the end of the time interval at block 410, the histogram defining a Lorenz plot is populated using the ($\delta RR_i$, $\delta RR_{i-1}$) points determined using only non-rejected RRIs at block 412.

Figure 9:
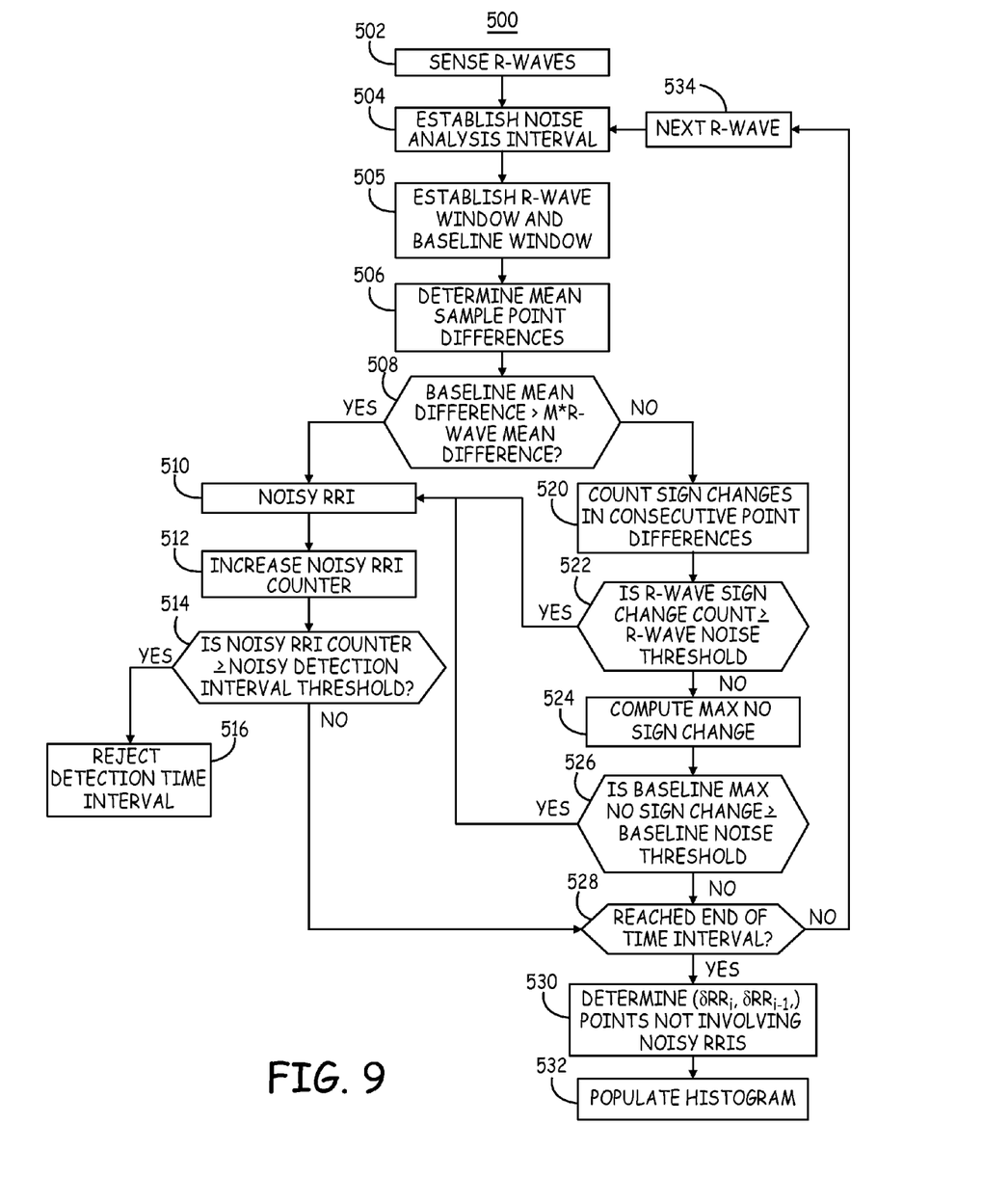
FIG. 9 is a flow chart of another method for detecting evidence of noise according to an alternative embodiment.

FIG. 9 is a flow chart 500 of another method for detecting noise according to an alternative embodiment. At block 502, R-waves are sensed from an EGM/ECG signal. At block 504, a noise analysis window is established relative to the sensed R-wave. The noise analysis window is separated into an R-wave window and a baseline window at block 505. The R-wave window may be approximately centered on the time of sensing the R-wave or an R-wave maximum peak amplitude and has a duration intended to generally encompass the sensed R-wave. The baseline window extends for a time period earlier than the R-wave window, and may begin at the start of the noise analysis window and end at the start of the R-wave window. The baseline window is intended to encompass a portion of the RRI that does not include the R-wave.

At block 506, the mean or median absolute difference in amplitude of consecutive signal sample points during the baseline window and during the R-wave window is determined. At block 508, the mean (or median) absolute difference between consecutive signal sample points determined during the baseline window is compared to the mean (or median) absolute difference between consecutive signal sample points during the R-wave window. Alternatively, the mean absolute difference for the baseline window may be compared to a predefined threshold or a percentage of the mean signal amplitude during the baseline window. If the mean absolute difference is high, for example greater than a percentage M of the mean absolute difference determined for the R-wave window, the signal-to-noise ratio is low. The high mean absolute difference between consecutive sample points during the baseline window indicates a noisy signal. The RRI during which the baseline window is established is detected as a noisy RRI at block 510.

In response to detecting a noisy RRI, a noisy RRI counter is increased by one count at block 512. The noisy RRI counter counts the number of RRIs determined to be noise contaminated during a given detection time interval. If the counter reaches a noisy detection time interval threshold, as determined at decision block 514, the current detection time interval is rejected in its entirety for use in classifying the atrial rhythm.

The threshold applied at decision block 514 may depend on the length of the detection time interval. If a large percentage or predetermined number of all RRIs during a given detection interval are found to be noisy, the detection time interval is rejected for use in rhythm detection and classification. A rhythm classification made upon expiration of a previous detection time interval may be maintained.

If the baseline mean difference between consecutive sample points does not exceed a threshold at decision block 508, additional noise analysis of the R-wave window and/or the baseline window may be performed. At block 520, consecutive amplitude differences are examined to determine if a sample point difference changes in sign (positive to negative or negative to positive) from one pair of consecutive sample points to the next pair of consecutive sample points. The two pairs of consecutive sample points may be defined by three sample points wherein the middle sample point is used in computing a first difference with a preceding sample point and a second difference with the immediately following sampling point. Alternatively the two pairs of sample points may be distinct. The sign of the first difference (negative, positive or zero) is compared to the sign of the second difference.

If both of the first and second differences are positive, or both are negative, the sign change counter is not increased at block 520. If one of the first and second differences is positive and one is negative, a sign change counter is increased at block 520. If one or both differences are zero, this zero difference is counted as a sign change, and the sign change counter is increased at block 520. A valid R-wave would produce a substantially increasing signal, e.g. positive-going, which would reach a peak and then produce a substantially decreasing signal, e.g. negative-going signal. During the substantially increasing or decreasing portions, a majority of the sample point differences will be either mostly positive or mostly negative with few or no sign changes between consecutively determined sample point differences. If frequent sign changes occur in the R-wave window, this variable signal may be detected as evidence of noise. A zero difference indicates a flat or inflection area of the signal. Few zero differences between consecutive sample points should exist during a valid R-wave; accordingly a zero difference is counted as a sign change.

If the sign change count during a given R-wave window reaches or exceeds a noise threshold at block 522, the sensed R-wave is detected as noise contaminated. One or both of the RRIs that immediately precede and immediately follow the sensed "R-wave" that has been detected as being noise may be classified as a noisy RRI at block 510. The noisy RRI counter is increased (by one or two) at block 512 and compared to a threshold for rejecting the current detection time interval at block 514.

In an alternative embodiment, the number of sign changes may be counted in both the R-wave window and the baseline window and compared. The number of sign changes in the R-wave window should be less than the number of sign changes during the baseline window. If the number of sign changes in the two windows is approximately equal or more sign changes are detected in the R-wave window than the baseline window, the associated RRI(s) may be detected as noisy RRI(s) at block 510.

If the number of sign changes in the R-wave window does not exceed a threshold at block 522, the process advances to block 524. At block 524, a maximum number of consecutive points that occur without a sign change between consecutive sample point differences is counted during the baseline window. If the baseline window is not contaminated by noise spikes, the number of consecutive points representing a continuously increasing or decreasing signal should be low. If noise is present, the maximum number of consecutive points occurring without a sign change between consecutive sample point differences will be higher than expected due to noise spikes.

As such, at decision block 526, the baseline window maximum "no sign change" count is compared to a baseline noise threshold. If the maximum number reaches a predetermined baseline noise threshold, the associated RRI is detected as a noisy RRI at block 510. The noisy RRI counter will be increased at block 512.

Alternatively, a maximum number of consecutive points occurring with no sign change between consecutive sample point differences ("max no sign change") may be determined for both the baseline window and the R-wave window. These maximum numbers may be compared to each other in order to ensure that the R-wave window has a significantly larger "max no sign change" count than the baseline window. In other embodiments, "max no sign change" counts for both the R-wave and the baseline windows may be compared to their own respective threshold to ensure the R-wave window has a relatively high "max no sign change" count and the baseline window has a relatively low "max no sign change" count.

This noise detection process continues by advancing to the next R-wave (block 534) until the end of the current detection time interval is reached as determined at block 528. While the decision blocks 508, 522, and 526 for detecting a noisy RRI are shown to occur serially in a particular order, it is recognized that the comparisons and criteria described in the foregoing may be applied in a different order, in parallel, alone or in any combination, for detecting noisy RRIs and for detecting a noisy detection time interval that is rejected in part or in whole, respectively, for use in classifying a cardiac rhythm. Furthermore, it is understood that in flow chart 500, and in other flow charts presented herein, the functions and outcomes described may still be successfully achieved when the operations described are performed in a different order than the specific order shown and some operations may be omitted, substituted, or performed alone or in different combinations than the combinations set forth in the illustrative embodiments presented herein.

Upon expiration of the detection time interval (block 528), the ($\delta RR_i$, $\delta RR_{i-1}$) data points are determined using RRIs that were not detected as noisy intervals at block 510 (if the entire detection time interval has not be rejected at block 516). The ($\delta RR_i$, $\delta RR_{i-1}$) data points that exclude any noisy RRIs are then used to populate a Lorenz plot area histogram at block 532 as described previously. Any ($\delta RR_i$, $\delta RR_{i-1}$) data point that would include a noisy interval is skipped and not counted in the histogram bins defining the Lorenz plot area.

In addition to counting the noisy RRIs at block 514, a total noise duration may be computed. For example, a total time duration or number of of consecutively detected noisy RRIs may be determined. If the duration or number of consecutively detected noisy intervals reaches a threshold, the detection time interval may be wholly rejected. The noisy RRI count (block 512) and the total noise duration or total consecutively rejected RRIs can be used alone or in any combination to reject a detection time interval for use in classifying a cardiac rhythm.

Various illustrative methods for detecting noise in a sensed event or in an RRI defined by sensed events have been described herein. It is recognized that numerous noise detection methods may be used and the noise detection method will depend in part on the cardiac signal being used to measure VCL and types of noise encountered by the implantable medical device system. Such methods may determine frequency content, amplitude content, or morphological features of the cardiac signal that correspond to non-physiological (or non-ventricular) signal content, which is detected as evidence of noise. One or more noise detection methods may be combined for use in rejecting VCLs found to contain or be associated with noise evidence.

Thus, an apparatus and method have been presented in the foregoing description with reference to specific embodiments. It is appreciated that various modifications to the referenced embodiments may be made without departing from the scope of the invention as set forth in the following claims.

The invention claimed is:

1. A method for determining a cardiac event, comprising:
   obtaining a signal comprising cardiac cycle length information in a patient;
   determining cardiac cycle lengths from the signal during an established time interval;
   detecting non-ventricular signal noise during the time interval;
   rejecting a cardiac cycle length corresponding to a time of the detected noise;
   determining a plurality of successive cardiac cycle length differences in response to only the cardiac cycle lengths not rejected during the time interval;
   and
   determining the cardiac event in response to the determined cycle length differences, wherein determining the cardiac event comprises:
     populating a two dimensional histogram for the established time interval with data points each having an x-coordinate and a y-coordinate and representing three consecutive non-rejected cardiac cycle length differences of the determined plurality of cycle length differences,
     wherein populating the histogram comprises skipping up to four possible data points involving the rejected cardiac cycle length, and
     determining the cardiac event from the populated histogram.

2. The method of claim 1, wherein detecting signal noise comprises comparing a cardiac cycle length during the established time interval to a noise detection threshold length.

3. The method of claim 2, further comprising determining a morphology metric from the signal in response to the cardiac cycle length being less than the noise detection threshold length.

4. The method of claim 1, wherein detecting signal noise comprises determining a signal frequency content.

5. The method of claim 1, wherein detecting signal noise comprises determining a signal amplitude content.

6. The method of claim 1, wherein detecting signal noise comprises computing signal sample point differences.

7. The method of claim 6, wherein detecting signal noise further comprises counting a number of changes in polarity between consecutive signal sample point differences.

8. The method of claim 7, further comprising detecting noise in response to the number of changes reaches a noise detection threshold.

9. The method of claim 7, further comprising counting a computed signal sample point difference of zero as a change in polarity.

10. The method of claim 1, further comprising determining one of a number of rejected cycle lengths and a duration of rejected cycle lengths, wherein determining the cardiac event comprises maintaining a previous cardiac event determination upon expiration of the time interval in response to at least one of the number and duration of rejected cycle lengths reaching a time interval rejection threshold.

11. A medical device for determining a cardiac event, comprising:
- a sensor to sense a signal comprising cardiac cycle length information in a patient; and
- a processor to receive the signal and configured to
- determine cardiac cycle lengths during an established time interval,
- detect non-ventricular signal noise during the time interval,
- reject a cardiac cycle length corresponding to a time of the detected noise,
- determine a plurality of successive cardiac cycle length differences from the cardiac cycle lengths not rejected during the time interval, and
- determine the cardiac event in response to the determined cycle length differences,
- the processor being configured to determine the cardiac event by:
  - populating a two dimensional histogram for the established time interval with data points each having an x-coordinate and a y-coordinate and representing three consecutive non-rejected cardiac cycle length differences of the determined plurality of cycle length differences,
  - wherein populating the histogram comprises skipping up to four possible data points involving the refected cardiac cycle length, and determining the cardiac event from the populated histogram.

12. The device of claim 11, wherein detecting the signal noise comprises comparing a cardiac cycle length during the time interval to a noise detection threshold length.

13. The device of claim 12, wherein the processor is further configured to determine a morphology metric from the signal in response to the cardiac cycle length being less than the noise detection threshold length.

14. The device of claim 11, wherein detecting signal noise comprises determining a signal frequency content.

15. The device of claim 11, wherein detecting signal noise comprises determining a signal amplitude content.

16. The device of claim 11, wherein detecting signal noise comprises computing signal sample point differences.

17. The device of claim 16, wherein detecting signal noise further comprises counting a number of changes in polarity between consecutive signal sample point differences.

18. The device of claim 17, wherein the processor is configured to detect noise in response to the number of changes reaching a noise detection threshold.

19. The device of claim 17, wherein the processor is configured to count two consecutive signal sample point differences of zero as a change in polarity.

20. The device of claim 11, wherein the processor is further configured to count a number of rejected cycle lengths, and maintain a previous cardiac event determination upon expiration of the time interval in response to the number of rejected cycle lengths reaching a time interval rejection threshold.

21. A non-transitory computer-readable medium storing a set of instructions which cause a processor of an implantable medical device to perform a method comprising:
- obtaining a signal comprising cardiac cycle length information in a patient;
- determining cardiac cycle lengths from the signal during an established time interval;
- detecting non-ventricular signal noise during the time interval;
- rejecting a cardiac cycle length corresponding to a time of the detected noise;
- determining a plurality of successive cardiac cycle length differences in response to only the cardiac cycle lengths not rejected during the time interval; and
- determining the cardiac event in response to the determined cycle length differences, wherein determining the cardiac event comprises:
  - populating a two dimensional histogram for the established time interval with data points each having an x-coordinate and a y-coordinate and representing three consecutive non-rejected cardiac cycle length differences of the determined plurality of cycle length differences,
  - wherein populating the histogram comprises skipping up to four possible data points involving the rejected cardiac cycle length, and determining the cardiac event from the populated histogram.

* * * * *